United States Patent [19]
Hansen et al.

[11] Patent Number: 5,478,845
[45] Date of Patent: Dec. 26, 1995

[54] PIPERIDINE DERIVATIVES

[75] Inventors: John B. Hansen, Jyderup; Frederik C. Grønvald, Vedæk; John P. Mogensen, Vanløse, all of Denmark

[73] Assignee: Novo Nordisk A/S, Bagsvaerd, Denmark

[21] Appl. No.: 247,388

[22] Filed: May 23, 1994

[30] Foreign Application Priority Data

May 26, 1993 [DK] Denmark .................................. 0605/93

[51] Int. Cl.$^6$ ....................... A61K 31/445; C07D 401/04
[52] U.S. Cl. ........................ 514/323; 514/217; 514/314;
514/233.8; 546/166; 546/169; 546/170;
546/187; 546/189; 546/198; 546/201; 544/105;
544/284; 540/586
[58] Field of Search ..................... 514/217, 314,
514/323, 233.8; 546/166, 169, 170, 187,
189, 198; 540/201, 480, 486; 544/105,
284

[56] References Cited

U.S. PATENT DOCUMENTS

| | | | |
|---|---|---|---|
| 5,001,134 | 3/1991 | Ferrand et al. | 514/321 |
| 5,100,902 | 3/1992 | Peglion et al. | 514/321 |
| 5,134,147 | 7/1992 | Peglion et al. | 514/300 |

FOREIGN PATENT DOCUMENTS

| | | |
|---|---|---|
| 0368388 | 10/1989 | European Pat. Off. . |
| 0402644 | 5/1990 | European Pat. Off. . |
| WO93/10742 | 6/1993 | WIPO . |

OTHER PUBLICATIONS

Yevich et al., J. Med. Chem., vol. 29, pp. 359–369 (1986).

*Primary Examiner*—Yogenbra N. Gupta
*Attorney, Agent, or Firm*—Steve T. Zelson; Elias J. Lambiris

[57] ABSTRACT

Piperidine derivatives of formula

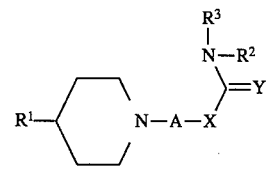

wherein A is straight or branched alkyl, alkoxy-alkyl, or alkenyl; X is O or NH; Y is O, S, NH, NCN, or N-alkyl; $R^1$ is 6-fluoro-1,2-benzisoxazol-3-yl, 6-fluoro-1H-indazol-3-yl, or 6-fluoro-1-methyl-1H-indazol-3-yl; $R^2$ is alkyl or phenyl; and $R^3$ is phenyl optionally substituted, or $R^3$ is

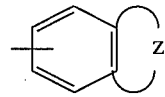

wherein Z represents a 5- or 6-membered heterocyclic ring; or $R^2$ and $R^3$ together with the nitrogen atom form a fused heterocyclic ring system; or pharmaceutically acceptable salts thereof are useful in the treatment of indications related to the CNS-system, cardiovascular system or to gastrointestinal disorders.

30 Claims, No Drawings

PIPERIDINE DERIVATIVES

The present invention relates to piperidine derivatives which are useful for treating CNS-system, cardiovascular system and/or gastrointestinal disorders, methods for preparing such compounds and pharmaceutical compositions containing them.

Much evidence has accumulated to suggest that neuroleptics exert their antipsychotic action by blocking dopamine (DA) receptors in the brain. In recent years, it has become clear that some neuroleptics (e.g. clozapine) show an atypical profile: the compounds are not only beneficial in treating patients, who respond poorly to classical neuroleptic therapy, but the compounds are also relatively devoid of extrapyrimidal side effects (EPS) commonly seen with classical neuroleptics (Ereshefsky et al., *Clin. Pharm* 8, 691–709, 1989). In this respect it has been speculated that atypical neuroleptics are working mainly by blocking socalled A10 mesolimbic DA systems (areas which are thought to be affected in psychosis), while the side effects of classical neuroleptics are produced by blockade of DA receptors in the motor areas of the brain (A9 DA system (Gudelsky, Psychopharmacology (Berl) 99: S 13-S 17, 1989) ). The antipsychotic effect of clozapine and related compounds might be due to its blockade of not only DA-receptors (D-1, D-2, D-3, D-4, D-5) but also 5HT-receptor subtypes ($5HT_2$-, $5HT_3$-, $5HT_{1C}$-, $5HT_{1A}$-), NA-$\alpha_1$-receptors, histamine and possibly other receptors.

Furthermore, $5HT_2$-blockade may also be important (Meltzer, Schizphr. Bull. 17: 263–87, 1991) to counteract the socalled negative symptoms of psychosis (delusions and social withdrawal) which are otherwise difficult to treat with conventional neuroleptics.

Compounds reducing 5-HT neurotransmission have been suggested to be useful for the treatment of various neurological and psychiatric diseases.

More specifically, the present invention relates to piperidine derivatives of the general formula (I)

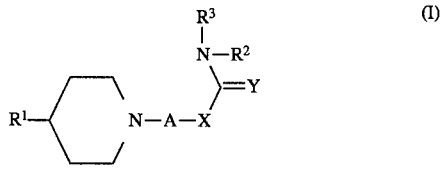

wherein

A is straight or branched $C_{1-6}$-alkyl, alkoxy-$C_{1-6}$-alkyl, or $C_{2-6}$-alkenyl; or, when $R^1$ is 6-fluoro-1-methyl-1H-indazol-3-yl, then A is also $C_{1-6}$-alkyl substituted with phenyl;

X is O or NH;

Y is O, S, NH, NCN, or N—$C_{1-6}$-alkyl;

$R^1$ is 6-fluoro-1,2-benzisoxazol-3-yl, 6-fluoro-1H-indazol-3-yl, or 6-fluoro-1-methyl-1H-indazol-3-yl;

$R^2$ is $C_{1-6}$-alkyl or phenyl; or, when $R^1$ is 6-fluoro-1-methyl-1H-indazol-3-yl, then $R^2$ is also hydrogen; and $R^3$ is phenyl optionally substituted with $C_{1-6}$-alkyl, halogen, $C_{1-6}$-alkoxy, or perhalomethyl, or $R^3$ is

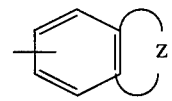

wherein

Z represents a 5- or 6-membered heterocyclic ring comprising one or more nitrogen-, oxygen-, or sulphur atoms; or $R^2$ and $R^3$ together with the nitrogen atom form a fused heterocyclic ring system;

and pharmaceutically acceptable salts thereof.

Physiologically and pharmaceutically acceptable salts of the compounds of the invention include acid addition salts formed with inorganic or organic acids, for example hydrochlorides, hydrobromides, sulphates, nitrates, oxalates, phosphates, tartrates, citrates, fumarates, maleates, succinates, and sulphonates e.g. mesylates. If desirable, selected salts may be subjected to further purification by recrystallization.

The invention includes within its scope all optical isomers of compounds of the general formula I and their mixtures including racemic mixtures thereof.

The term "$C_{1-6}$-alkyl" as used herein, alone or in combination, refers to a straight or branched, saturated hydrocarbon chain having 1–6 carbon atoms such as methyl, ethyl, n-propyl, isopropyl, n-butyl, tert.butyl, n-pentyl, neopentyl, n-hexyl and 2,2-dimethylpropyl.

The term "alkoxy" as used herein, alone or in combination, refers to a monovalent substituent comprising a $C_{1-6}$-alkyl group linked through an ether oxygen having its free valence bond from the ether oxygen, e.g. methoxy, ethoxy, propoxy, butoxy, pentoxy.

The term "$C_{2-6}$-alkenyl" as used herein refers to an unsaturated hydrocarbon chain having 2–6 carbon atoms and one double bond such as vinyl, 1-propenyl, allyl, isopropenyl, n-butenyl, n-pentenyl and n-hexenyl.

The term "halogen" means fluorine, chlorine, bromine and iodine.

The term "perhalomethyl" means —$CF_3$, —$CCl_3$, —$CBr_3$ and —$Cl_3$.

The term "5- or 6-membered heterocyclic ring" as used herein refers to a monocyclic unsaturated or saturated ring containing one or more hetero atoms selected from nitrogen, oxygen and sulphur and having 5 or 6 members, e.g. pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl, thiazolyl, 1,3-dioxolanyl, 1,4-dioxolanyl.

The term "fused heterocyclic ring system" as used herein refers to a multiple heterocyclic ring system preferably having 2 or 3 fused unsaturated or saturated rings in a linear or branched arrangement.

Accordingly, when $R^2$ and $R^3$ together with the nitrogen atom form a fused heterocyclic ring system, the group —N($R^2$)($R^3$) can preferably be a dibenzazepine, indoline, 1,2,3,4-tetrahydroquinoline, methylenedioxyindoline, methylenedioxy-1,2,3,4-tetrahydroquinoline, or a 3,4-dihydro-2H-1,4-benzoxazine group.

In a preferred embodiment of the invention, $R^3$ is selected from benzthiazolyl, benzimidazolyl, benzisoxazolyl, 1H-indazolyl, benzofuranyl, indolyl, 3H-indolyl, indolinyl, benzothienyl, quinolinyl, 1,2,3,4-tetrahydroquinolinyl, quinazolinyl and 3,4-methylenedioxyphenyl.

In another preferred embodiment of the invention, A is a straight or branched $C_{1-6}$-alkyl, preferably ethyl, propyl or n-butyl, optionally substituted with phenyl; X is Q and Y is O.

The substituent $R^1$ is selected from

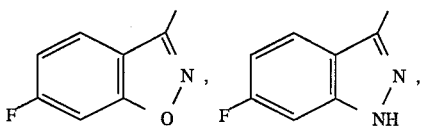

i.e. 6-fluoro-1,2-benzisoxazol-3-yl, 6-fluoro-1H-indazol-3-yl, and 6-fluoro-1-methyl-1H-indazol-3-yl.

Preferred compounds of the invention are:
4-(6-Fluoro-1,2-benzisoxazol-3-yl)-1-(3-((1,2,3,4-tetrahydroquinolin-1-yl)carbonyloxy) propyl)piperidine;
4-(6-Fluoro-1,2-benzisoxazol-3-yl)-1-(3-(N-ethyl-N-(3,4-methylenedioxyphenyl) carbamoyloxy) propyl) piperidine;
4-(6-Fluoro-1,2-benzisoxazol-3-yl)-1-(3- (N-methyl-N-phenylcarbamoyloxy)propyl)piperidine;
4-(6-Fluoro-1,2-benzisoxazol-3-yl)-1-(3-(N-(6-benzothiazolyl)-N-methylcarbamoyloxy) propyl)piperidine;
4-(6-Fluoro-1,2-benzisoxazol-3-yl)-1-(3-(N-methyl-N-(3,4-methylenedioxyphenyl) carbamoyloxy)propyl)piperidine;
4-(6-Fluoro-1,2-benzisoxazol-3-yl)-1-(3-((indolin-1-yl)carbonyloxy)propyl)piperidine;
4-(6-Fluoro-1,2-benzisoxazol-3-yl)-1-(2-((1,2,3,4-tetrahydroquinolin-1-yl)carbonyloxy) propyl)piperidine;
1-(2-(3,4,5-trimethoxyphenylcarbamoyloxy-1-propyl)-4-(6-fluoro-1-methyl-1H -indazol-3-yl)piperidine;
1-[2((10,11-dihydro-5H-dibenz[b,f]azepin-5-yl)carbamoyloxy)propyl]-4-(6 -fluoro-1,2-benzisoxazol-3-yl)piperidine;
1-(3-((10,11-dihydro-5H-dibenz[b,f]azepin-5-yl)carbonyloxy)propyl]-4-(6 -fluoro-1,2-benzisoxazol-3-yl)piperidine;
4-(6-fluoro-1-methyl-1H-indazol-3-yl)-1-(3-((1,2,3,4-tetrahydroquinolin-1-yl) carbonyloxy)-propyl)piperidine;
1-[3-(3,4-methylenedioxophenylcarbamoyloxy)-propyl] -4-(6-fluoro-1-methyl -1H-indazol-3-yl)-piperidine;
1-[2-(phenyl)-2-(3,4,5-trimethoxyphenylcarbamoyloxy) ethyl] 4-(6-fluoro-1 -methyl-1H-indazol-3-yl)-piperidine;
4-(6-Fluoro-1,2-benzisoxazol-3-yl)-1-(3-((6,7-methylenedioxy-1,2,3,4 -tetrahydroquinolin-1-yl)carbonyloxy)propyl)piperidine;
4-(6-Fluoro-1,2-benzisoxazol-3-yl)-1-(2-((6,7-methylenedioxy-1,2,3,4 -tetrahydroquinolin-1-yl)carbonyloxy)ethyl)piperidine;
4-(6-Fluoro-1,2-benzisoxazol-3-yl)-1-(4-((6,7-methylenedioxy-1,2,3,4 -tetrahydroquinolin-1-yl)carbonyloxy)butyl)piperidine;
4-(6-Fluoro-1,2-benzisoxazol-3-yl)-1-(3-((5,6-methylenedioxyindoline-1-yl) carbonyloxy) -2-phenylpropyl)piperidine;
4-(6-Fluoro-1,2-benzisoxazol-3-yl)-1-(3-((5,6-methylenedioxyindoline-1-yl)carbonyloxy) propyl)piperidine;
1-[3-(3,4,5-trimethoxyphenylcarbamoyloxy)-propyl]-4-(6-fluoro-1-methyl-1H -indazol-3-yl)piperidine, or pharmaceutically acceptable acid addition salts of these compounds.

The compounds of the present invention demonstrate high affinity for various receptor subtypes including the $5HT_2$-, the dopamine $D_1$- and $D_2$-receptors or a combination of these.

Accordingly, in another aspect the invention relates to a compound of the general formula (I) or a pharmaceutically acceptable acid addition salt thereof for use as a therapeutically acceptable substance, preferably for use as a therapeutically acceptable substance in the treatment of CNS-system disorders, cardiovascular disorders or gastrointestinal disorders.

Furthermore, the invention also relates to the use of the inventive compounds of formula (I) as medicaments useful for treating CNS-system, cardiovascular system and gastrointestinal disorders, such as treatment of anxiety, sleep disorders, depression, psychosis, schizophrenia, migraine, ischemic neuronal damage, asthma, hypertension, urticaria, analgesia and emesis.

In yet another aspect, the invention relates to a method of preparing the above mentioned compounds. In a variant a) of the method of the invention, a compound of formula (11)

wherein Y, $R^2$ and $R^3$ have the meanings set forth above, and Q is a leaving group, is reacting with a compound of formula (III)

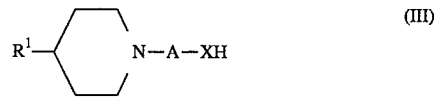

wherein A, X and $R^1$ have the meanings set forth above to form a compound of formula I.

For instance the N-ethyl-N-(3,4-methylenedioxyphenyl)carbamoyl chloride prepared by treatment of N-ethyl-3,4-methylenedioxyaniline with phosgene in the presence of triethylamine, may be reacted with the desired piperidine alkylamine or piperidine alkylhydroxy intermediate to obtain the desired urea or carbamate of formula I.

Compounds of formula I, wherein X is —NH— and Y is =NH, =NCN or =N— $C_{1-6}$-alkyl are prepared by standard procedures as described in e.g. H. J. Petersen et al., J.Med.Chem. (1978) 21,773–781, and R. Lee Webb et al., J. Heterocyclic Chem. 24, 275 (1987).

In a variant b) of the method of the invention a compound of formula (IV)

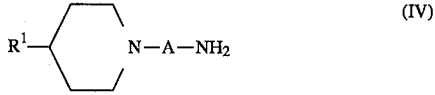

wherein A and $R^1$ have the meanings set forth above, is reacting with a compound of formula (V)

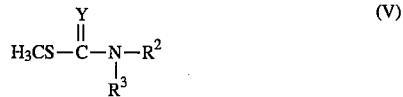

wherein $R^2$ and $R^3$ have the meanings set forth above, and Y is =NH, =NCN or =N—$C_{1-6}$-alkyl.

In a variant c) of the method of the invention, a compound of formula (III), wherein X is —NH— and A and $R^1$ have the meanings set forth above, is reacting with a compound of formula (VI)

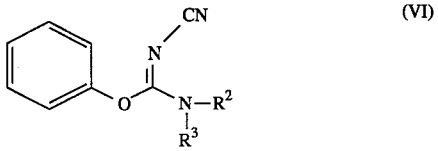
(VI)

wherein $R^2$ and $R^3$ have the meanings set forth above, prepared by the method described in R. Lee Webb and C. S. Labaw, J. Heterocyclic Chem. 19, 1205 (1982) from $R^2$—NH and N-cyanodiphenoxyimidocarbonate, and in a variant d) of the method of the invention, a compound of formula VII

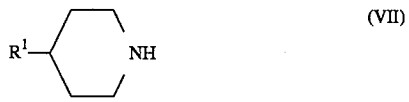
(VII)

wherein $R^1$ has the meaning set forth above, is reacted using routine procedures with a compound of formula VIII

(VIII)

wherein $R^2$, $R^3$, A has the meaning set forth above and L is a suitable leaving group, e.g. halogen, tosylate or mesylate.

Compounds of formula (III), wherein $R^1$, A and X have the meanings set forth above, have been prepared by alkylating the known piperidine derivative (VII) (J. T. Strupczewski et al., J.Med.Chem., 28, 761–769 (1985))

(VII)

wherein $R^1$ has the meaning set forth above, using standard procedures.

The compounds of the present invention have been tested for binding to various CNS receptor subtypes in vitro in mice.

Detailed conditions for the in vitro assays are described below:

TEST 1: In Vitro Inhibition of DOPAMINE D2 Receptor Binding

Method Description

Principle:

Radioactive-labelled ligand $^3$H-Spiroperidol is incubated with isolated cell-membrane fragments at 37° C. for a given period of time. Following completed incubation, the incubate is filtered through GF/B filters which are rinsed following filtration to remove unspecifically adhered radioactivity. As opposed to low-molecular compounds, membrane fragments are not rinsed through the filters, the radioactivity bound to the filters is indicative of the amount of ligand bound specifically as well as nonspecifically to the membranes.

Tissue preparation:

The procedure is performed in ice bath. Polytron kinematica is rinsed with milli-Q—$H_2O$ before and after use. Male Wistar rats, 150–200 g are decapitated, striatum is removed quickly and weighed (approx. 50 mg). Striatum is transferred to a centrifuging vial containing 10 ml ice-cold D2 buffer. Homogenization is performed applying polytron kinematica (homogenizer) setting 6 for 20 sec. The homogenizer is rinsed with 10 ml D2 buffer in another centrifuging vial. The 10 ml rinsing buffer is added to the tissue vial. Centrifugation at 18,000 rpm for 10 min. at 4° C. Final pellet is transferred to 1,000×vol. of same buffer. (Ex. 50 mg striatum in 50 ml D2 buffer). Can be stored at 0° C. for at least 4 hours. Note that the tissue must be monogeneous (uniform) before use. If not, brief homogenization is performed.

Assay:

2,500/µl tissue (homogeneous)

25 µl $^3$H-Spiroperidol (0.05 nM) 25/µl test substance/ $H_2O$/blind (Domperidone 0.2/µM) Incubation for 20 min. at 37° C.—10 min. on ice bath.

10 ml ice-cold 0.9% NaCl is added to the tubes and filtered through GF/B filters (use gloves). This procedure is repeated. The filters are placed in counting vials and 4 ml opti-flour is added (perform in fume cupboard, use gloves). Counting is performed at window 0-19 of the beta-counter (Pachard). Note that receptor box and lid are rinsed thoroughly in $H_2O$ after use to avoid contamination. Further, the analytical site is cleaned carefully every day after use.

Test substances:

Dissolved in $H_2O$, EtOH, MeOH or DMSO and further diluted in $H_2O$. The D2 binding will stand concentrations of up to approx. 20% of these solvents without affecting the binding. Most stock solutions are stable at 4° C., attention is, however, paid to any precipitation, change in colour etc. Test-substance dilutions are always made fresh every day. When weighing out test substances, it is attempted to weigh out approx. 1 mg of substance. Less than 0.8 mg must never be weighed out and only infrequently more than 2 mg (for economy reasons), dependent, however, on conc./assay.

Results:

The test result is shown in Table I as $IC_{50}$ indicating the concentration inhibiting specific binding by 50%.

TEST 2: In Vitro Inhibition of DOPAMINE D1 Receptor Binding

Method Description

Principle:

Radioactive-labelled ligand $^3$H-SCH 23390 is incubated with isolated cell-membrane fragments in incubation buffer at 30° C. for a given period of time. Following completed incubation, the incubate is filtered through GF/B filters, which are rinsed following filtration to remove unspecifically adhered radioactivity. As opposed to low-molecular compounds, membrane fragments are not rinsed through the filters, the radioactivity bound to the filters indicates the amount of ligand bound specifically as well as nonspecifically to the membranes.

Tissue preparation:

Male Wistar rats, 150–200 g are decapitated. Striatum is removed quickly, weighed (approx. 50 mg) and carefully homogenized in 100×vol. of buffer I applying glass/teflon homogenizer 10 up/down strokes. Ex.: 50 mg striatum is homogenized in 5,000/µl buffer I. The homogenate is centrifuged at 18,000 rpm for 20 min. at 4° C., and the supernate is decanted. This step is performed three times, and each time the pellet is resuspended and homogenized in 100×vol. of buffer I. Following the third centrifugation, the pellet is suspended in 100×vol. of resuspension buffer and homogenized. The tissue is now ready for use. The tissue is stable at 0° C. for 8 hours.

Assay:
  600/µl incubation buffer
  100 µl $^3$H-SCH 23390 (0.2 nM)
  100 µl tissue
  200 µl test substance/H$_2$O/blind (cis-flupentixol 2 µM)
  Incubation for 60 min. at 30° C.

10 ml of ice-cold 0.9% NaCl is added to the tubes. Filtration is performed through GF/B filters (use gloves). This procedure is repeated. Filters are placed in counting vials and 4 ml opti-flour is added (perform in fume cupboard, use gloves) and counting is performed at window 0-19 of the beta-counter (Pachard). Note that receptor box and lid are rinsed thoroughly in H$_2$O after use to avoid contamination. Further, the analytical site is cleaned carefully every day after use.

Test substances:
Dissolved in H$_2$O, EtOH, MeOH or DMSO and further diluted in H$_2$O. The D1 binding will stand concentrations of up to approx. 20% of these solvents without affecting the binding. Most stock solutions are stable at 4° C. Attention should, however, be paid to any precipitation, change in colour etc. Test-substance dilutions are always made fresh every day. When weighing out test substances, it is attempted to weigh out approx. 1 mg of substance. Less than 0.8 mg must never be weighed out and only infrequently more than 2 mg (for economy reasons), dependent, however, on conc./assay.

Results:
The test result is shown in Table I as IC$_{50}$ indicating the concentration inhibiting specific binding by 50%.

TEST 3: In Vitro Inhibition of 5HT$_2$-Receptor Binding

Method Description

Principle:
Radioactive-labelled ligand $^3$H-Ketanserine is incubated with isolated cell membrane fragments at 37° C. for a given period of time. Following completed incubation, the incubate is filtered through GF/B filters, which are rinsed following filtration to remove unspecifically adhered radioactivity. As opposed to low-molecular compounds, membrane fragments are not rinsed through the filters, the radioactivity bound to the filters indicates the amount of ligand bound specifically as well as nonspecifically to the membranes.

Tissue preparation:
The preparation is made in ice bath. Polytron kinematica is rinsed with milli-Q—H$_2$O before and after use. Male Wistar rats, 150–200 g are decapitated. Frontal cortex is removed quickly and weighed (approx. 200 mg). Frontal cortex is added to centrifuging vial containing 10 ml ice-cold D2 buffer. Homogenization applying polytron kinematica (homogenizer) setting 6 for 20 sec. The homogenizer is rinsed with 10 ml D2 buffer in another centrifuging vial. The 10 ml rinsing buffer is added to the tissue vial. Centrifuged at 18,000 rpm for 10 min. at 4° C. Final pellet is transferred to 125×vol. of same buffer. (Ex 200 mg in 25 ml D2 buffer). Can be stored for approx. 30 min. at 0° C.

Assay:
  1250/µl tissue
  25/µl $^3$H-Ketanserine (0.4 nM)
  25/µl test substance/H$_2$O/blind cyproheptadine (2/µM)
  Incubation for 15 min. at 37° C.

10 ml ice-cold 0.9% NaCl is added to the tubes. Filtration is performed through GF/B filters (use gloves). This procedure is repeated. The filters are placed in counting vials and 4 ml opti-flour is added (prepare in fume cupboard, use gloves). Counting at window 0-19 of the beta-counter (Pachard). Note that receptor box and lid are rinsed thoroughly in H$_2$O after use to avoid contamination. Further, the analytical site is cleaned carefully every day.

Test substances:
Dissolved in H$_2$O, EtOH, MeOH or DMSO and further diluted in H$_2$O. The 5HT$_2$ binding will stand concentrations of up to approx. 5% of these solvents without affecting the binding. Most stock solutions are stable at 4° C. Attention should, however, be paid to any precipitation, change in colour etc. Test-substance dilutions are always made fresh every day. When weighing out test substances, it is attempted to weigh out approx. 1 mg of substance. Less than 0.8 mg must never be weighed out and only infrequently more than 2 mg (for economy reasons), dependent, however, on conc./assay.

Results:
The test result is shown in Table I as IC$_{50}$ i.e. the concentration inhibiting specific binding by 50%.

TABLE I

| | Results from in vitro tests | | |
|---|---|---|---|
| Compound of | TEST 1 IC$_{50}$ (nM) | TEST 2 IC$_{50}$ (nM) | TEST 3 IC$_{50}$ (nM) |
| Example 2 | 18 | 30 | 6.7 |
| Example 3 | 8.9 | 43 | 6.9 |

The compounds of the invention, together with a conventional adjuvant, carrier, or diluent, and if desired a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compound of the invention is dispensed in unit dosage form comprising 0.05–100 mg in a pharmaceutically acceptable carrier per unit dosage.

A typical tablet which may be prepared by conventional tabletting techniques contains:

| | |
|---|---|
| Active compound | 1.0 mg |
| Lactosum | 67.8 mg Ph. Eur. |
| Avicel ® | 31.4 mg |
| Amberlite ® IRP 88 | 1.0 mg |
| *Magnesii stearas* | 0.25 mg Ph. Eur. |

The following non-limiting examples illustrate the invention.

EXAMPLE 1

4-(6-Fluoro-1,2-benzisoxazol-3-yl)-1-(3-((1,2,3,4-tetrahydroquinolin-1-yl)carbonyloxy)propyl)piperidine, hydrochloride A. To phosgene (58 mmol, 30 ml 1.93M in toluene) and methylene chloride (50 ml) stirred at 0° C. was added during 40 min. 1,2,3,4-tetrahydroquinoline (6.66 g, 50 mmol) and triethylamine (7.08 g, 70 mmol) in 50 ml methylene chloride. The mixture was then stirred at 0° C. for 1 h and poured into 800 ml petroleum ether. This mixture was washed three times with 50 ml 5N $H_2SO_4$ and once with saturated NaCl. The organic phase was dried over $Na_2SO_4$ and concentrated in vacuo giving 8.6 g of 1-(1,2,3,4-tetrahydro)quinolinecarbonyl chloride as an oil.

B. 3-(4-(6-Fluoro-1,2-benzisoxazol-3-yl)piperidino)propanol (280 mg, 1 mmol) was added to NaH (100 mg 50% in mineral oil, 1.5 mmol) in 5 ml dry DMF at 0° C. under nitrogen atmosphere. The mixture was stirred at 0° C. for 30 min. and for 90 min. at room temperature, whereupon 1-(1,2,3,4-tetrahydro)quinolinecarbonyl chloride (300 mg, 1.5 mmol) in 2 ml dry DMF was added during 5 min. The mixture was stirred consecutively at room temperature for 16 h, and at 60° C. for 1 h, and then separated between water and ether. The organic phase was evaporated, and the resulting oil was purified by column chromatography (silica gel; ethyl acetate, methanol (4:1, v/v)) and then dissolved in absolute ethanol (2 ml). Addition of etheral hydrochloric acid precipitated the title compound (300 mg) which was recrystallized in ethanol and acetone, methanol (9:1) to give 200 mg of white crystals. M.p. 188°–190° C.

MS (70 eV): 437 ($M^+$, 7.5), 278 (6), 233 (23), 140 (33), 96 (100).

EXAMPLE 2

4-(6-Fluoro-1,2-benzisoxazol-3-yl)-1-(3-(N-ethyl-N-(3,4-methylenedioxyphenyl)carbamoyloxy)propyl piperidine, oxalate A. By following the procedure described in example 1A, N-ethyl-3,4-methylenedioxyaniline (1.65 g, 10 mmol) was reacted with phosgene to give 1.5 g N-ethyl-N-(3,4-methylenedioxyphenyl)carbamoylchloride. M.p. 68°–69° C.

B. To 3-(4-(6-Fluoro-1,2-benzisoxazol-3-yl)piperidino)propanol (280 mg, 1 mmol) in 15 ml dry THF stirred under nitrogen atmosphere, was added n-butyl lithium (0.9 ml 1.6M in hexane, 1.5 mmol). The mixture was stirred at room temperature for 1.5 h, whereupon N-ethyl-N-(3,4-methylenedioxyphenyl)carbamoyl chloride (340 mg, 1.5 mmol) in 15 ml dry THF was added. The mixture was stirred at room temperature for 16 h and then separated between water and ethyl acetate. The organic phase was washed with $H_2O$ and saturated NaCl, dried over $Na_2SO_4$ and concentrated in vacuo. The product was purified by column chromatography (silica gel, ethyl acetate, methanol (4:1, v/v)) and dissolved in 2 ml acetone. Addition of oxalic acid precipitated the title compound which was recrystallized from ethanol, methanol (20:1) to give 250 mg. M.p. 180°–182° C.

MS (70 eV): 469 ($M^+$, 82%), 331 (31), 250 (45), 233 (100).

EXAMPLE 3

4-(6-Fluoro-1,2-benzisoxazol-3-yl)-1-(3-(N-methyl-N-phenylcarbamoyloxy)propyl)piperidine, oxalate By following the procedure described in example 2B, 3-(4-(6-fluoro-1,2-benzisoxazol-3-yl)piperidino)propanol (278 mg, 1 mmol) was reacted with N-methyl-N-phenylcarbamoyl chloride (190 mg, 1.12 mmol) to give 330 mg of the title compound upon recrystallization from 2-propanol. M.p. 174°–176° C.

MS (70 eV): 411 ($M^+$, 46%), 273 (27), 233 (100).

EXAMPLE 4

4-(6-Fluoro-1,2-benzisoxazol-3-yl)-1-(3-(N-(6-benzothiazolyl)-N-methylcarbamoyloxy)propyl)piperidine, oxalate A. 6-Aminobenzothiazole (1.5 g, 10 mmol) and triethylamine (1.4 g, 14 mmol) was suspended in 30 ml dry toluene at 10° C. Trifluoroacetic acid anhydride (2.5 g, 12 mmol) in 5 ml dry toluene was added under stirring at 10°–15° C. during 30 min., whereunder the mixture was gradually solubilized. The mixture was poured into 100 ml ether, and then washed five times, each time with 15 ml $H_2O$. The organic phase was dried over $Na_2SO_4$ and concentrated to a volume of 10 ml. Addition of petroleum ether precipitated 2.05 g 6-trifluoroacetamido-benzothiazole as white crystals. M.p. 155°–156° C.

B. To 6-Trifluoroacetamidobenzothiazole (1.97 g, 8 mmol) in 40 ml dry acetone was added methyl iodide (4.54 g, 32 mmol) and then KOH (2.1 g, 32 mmol). The mixture was refluxed for 40 min. and concentrated in vacuo. The product was taken up in 40 ml $H_2O$, refluxed for 40 min. and extracted with methylene chloride. The organic phase was washed with water, dried over $Na_2SO_4$ and concentrated in vacuo. The product was purified by flash chromatography (silica gel, methylene chloride) to give 250 mg 6-methylamino-benzothiazole.

C. By following the procedure described in example 2B, 3-(4-(6-fluoro -1,2-benzoisoxazol-3-yl)piperidino)propanol (680 mg, 3 mmol) was reacted with 6-methylaminobenzothiazole (560 mg, 2 mmol) giving 180 mg of the title compound. M.p. 156°–162° C.

MS (70 eV): 468 (M$^+$, 25%) 330 (13), 249 (22), 233 (48), 96 (100).

EXAMPLE 5

4-(6-Fluoro-1,2-benzisoxazol-3-yl)-1-(3-(N-methyl-N-(3,4-methylenedioxyphenyl)carbamoyloxy) propyl)piperidine, hydrochloride A. By following the procedure described in example 1A N-methyl-3,4-methylenedioxyaniline (N. J. Houlihan et al., J.Het. Chem. 19, 1453 (1982)) (3.02 g, 20 mmol) was reacted with phosgene to give 3.0 g N-methyl-N -(3,4-methylenedioxyphenyl)carbamoylchloride. M.p. 71°–73° C.

B. By following the procedure described in example 2B 3-(4-(6-fluoro -1,2-benzisoxazol-3-yl)piperidino)propanol (278 mg, 1 mmol) was reacted with N-methyl-N-(3,4-methylenedioxyphenyl)carbamoylchloride (240 mg, 1.12 mmol) to give 170 mg of the title compound. M.p. 126°–129° C.

MS (70 eV): 455 (M$^+$, 64%), 317 (22), 237 (36), 233 (50), 96 (100).

EXAMPLE 6

4-(6-Fluoro-1,2-benzisoxazol-3-yl)-1-(3-((indolin-1-yl) carbonyloxy)propyl)piperidine A. By following the same procedure described in example 1 A, 2,3-dihydroindole (5.95 g, 50 ml) was reacted with phosgene to prepare 3.2 g 1-(2,3-dihydro)indole carbonyl chloride. M.p. 74°–75° C.

B. By following the same procedure described in example 2B 3-(4-(6 -fluoro-1,2-benzisoxazol-3-yl)piperidino)propanol (280 mg, 1 mmol) was reacted with 1-(2,3-dihydro)indole carbonyl chloride (270 mg, 1.5 mmol) to give 120 mg of the title compound. M.p. 218°–219° C.

MS (70 eV): 423 (M$^+$, 30%), 285 (21), 233 (60), 204 (52), 96 (100).

EXAMPLE 7

4-(6-Fluoro-1,2-benzisoxazol-3-yl)-1-(2-((1,2,3,4-tetrahydroquinolin-1-yl) carbonyloxy)-1-propyl)piperidine, hydrochloride A solution of 1-(2-hydroxyprop-1-yl)-4-(6-fluoro-1,2-benzisoxazol-3-yl)piperidine (278 mg; 1 mmol) in 20 ml dry THF was cooled to −70° C., under nitrogen atmosphere was added N-butyl litium (3M in hexane, 0.4 ml; 1.2 mmol). After 0.5 h a solution of 1,2,3,4-tetrahydroquinolin-1-carbonylchloride (235 mg; 1.2 mmol) in 10 ml dry THF was added dropwise. The reaction was stirred at −70° C. for 1 h and then 16 h at room temperature, concentrated in vacuo and purified by chromatography on silica gel 60 with ethyl acetate:methanol (9:1, v/v) as eluent.

The appropriate fractions was collected. The solvent was evaporated in vacuo to give an oily residue which was dissolved in acetone (5 ml). A 2M solution of hydrogen chloride in diethylether (1 ml) was added at room temperature whereby a white precipitate was formed. The solid was collected and air dried to give 200 mg (42%) of the title compound. M.p. 76°–79° C.

$^1$H-NMR (CDCl$_3$-ppm): 1.3 (d, 3H), 2.0 (m, 6H), 2.1–2.5 (m, 3H), 2.69 (dd, 1H), 2.8 (t, 2H), 3.08 (m, 3H), 3.71 (m, 1H), 3.88 (m, 1H), 5.15 (m, 1H), 6.95 (m, 5H), 7.52 (q, 1H), 7.78 (dd, 1H).

EXAMPLE 8

1-(2-(3,4,5-trimethoxyphenylcarbamoyloxy)-1-propyl)-4-(6-fluoro-1-methyl-1H -indazol-3-yl)piperidine A. A mixture of 4-(6-fluoro-1-methyl-1H-indazol-3-yl)piperidine (2 g; 8.6 mmol) and propylene oxide (1 g; 58 mmol) in 10 ml acetonitrile was heated to 50° C. in an autoclave for 4 days. The cooled reaction mixture was concentrated in vacuo, and purified by chromatography on silica gel 60 with ethyl acetate:methanol (3:1, v/v) as eluent.

Concentration of the appropriate fractions gave 600 mg (23%) of 1-(2 -hydroxyprop-1-yl)-4-(6-fluoro-1-methyl-1H-indazol-3-yl)piperidine.

$^1$H-NMR (CDCl$_3$-ppm): 1.15 (d, 3H), 1.95–2.55 (m, 8H), 2.87–3.24 (m, 3H), 3.85 (m, 1H), 3.98 (s, 3H), 6.83 (dt, 1H), 6.98 (dd, 1H), 7.65 (q, 1H).

B. To a solution of 1-(2-hydroxyprop-1-yl)-4-(6-fluoro-1-methyl-1H -indazol-3-yl)piperidine (200 mg; 0.69 mmol) in 5 ml dry DMF was added 3,4,5-trimethoxyphenylisocyanate (200 mg; 0.96 mmol) in 3 ml dry DMF. The reaction mixture was heated to 100° C. for 2 h, followed by cooling to room temperature and addition of a mixture of 25 ml water and 150 ml ether. The reaction mixture was filtered and separated. The ether phase was washed with water, brine, dried with sodium sulphate and concentrated in vacuo. The crude product was purified by chromatography on silica gel 60 with ethyl acetate:methanol (9:1, v/v) as eluent. Concentration of the appropriate fractions gave 100 mg (29%) of the title compound. M.p. 74°–77° C.

$^1$H-NMR (CDCl$_3$-ppm): 1.31 (d, 3H), 1.91–2.33 (m, 5H), 2.41 (dd, 1H), 2.7 (m, 1H), 3.05 (m, 2H), 3.2 (d, 1H), 3.79 (s, 3H), 3.85 (s, 6H), 3.92 (s, 3H), 5.15 (m, 1H), 6.7 (s, 2H), 6.79 (dt, 1H), 6.95 (dd, 1H), 7.59 (q, 1H).

EXAMPLE 9

1-[2((10,11-dihydro-5H-dibenz[b,f]azepin-5-yl) carbamoyloxy)-1-propyl]-4-(6 -fluoro-1,2-benzisoxazol-3-yl)piperidine, oxalate Starting from 1-(2-hydroxyprop-1-yl)-4-(6-fluoro-1,2-benzisoxazol-3-yl)piperidine (278 mg; 1 mmol), 3M N-butyl lithium in hexane (0.4 ml; 1.2 mmol) and 10,11-dihydro-5H-dibenz[b,f]azepine-5-carbonyl chloride (309 mg; 1.2 mmol) using the procedure described in example 7 was prepared the isolated free base of the title compound. The isolated free base was dissolved in ethyl acetate (5 ml). A solution of oxalic acid (45 mg; 0.5 mmol) in ethyl acetate (3 ml) was added at room temperature whereby a white precipitate was formed. The solid was collected and air dried to give 90 mg (15%) of the title compound. M.p. 171°–172° C.

MS/EI (70 eV): M/Z 499 (3%, M+), 260 (100%), 233, 194, 138, 122, 96.

EXAMPLE 10

1-[3-((10,11-dihydro-5H-dibenz[b,f]azepin-5-yl) carbonyloxy)propyl]-4-(6 -fluoro-1,2-benzisoxazol-3-yl)piperidine, oxalate Starting from 1-(3-hydroxyprop-1-yl)-4-(6-fluoro-1,2-benzisoxazol-3-yl)piperidine (278 mg; 1 mmol), 3M N-butyl lithium in hexane (0.4 ml; 1.2 mmol) and 10,11-dihydro-5H-dibenz[b,f]azepine-5-carbonyl chloride (309 mg; 1.2 mmol) using the procedure described in example 9 was prepared 100 mg (17%) of the title compound.

Analysis: $C_{30}H_{30}N_3O_3F$, $C_2H_2O_4$
Cal.: C 65.2% H 5.5% N 7.1%
Found: C 65.1% H 5.6% N 6.9%

EXAMPLE 11

4-(6-fluoro-1-methyl-1H-indazol-3-yl)-1-(3-((1,2,3,4-tetrahydroquinolin-1-yl) carbonyloxy)-propyl)piperidine, hydrochloride A. A mixture of 4-(6-fluoro-1-methyl-1H-indazol-3-yl)piperidine (5.0 g; 0.02 mol), potassium carbonate (8.28 g; 0.06 mol), 3-bromopropanol (2.98 g; 0.02 mol) and acetone (100 ml) was stirred and refluxed for 20 h. The reaction mixture was filtered, concentrated in vacuo and purified by chromatography on silica gel 60 with ethyl acetate:methanol (8:2, v/v) as eluent. Concentration of the appropriate fractions afforded 2.1 g (34%) of 4-(6-fluoro-1-methyl-1H-indazol-3-yl)-1-(3-hydroxypropyl)piperidine.

Analysis: $C_{16}H_{22}N_3OF$
Cal.: C 65.96% H 7.61% N 14.42%
Found: C 65.98% H 7.76% N 14.14%

B. Starting from 4-(6-fluoro-1-methyl-I H-indazol-3-yl)-1-(3-hydroxypropyl)piperidine (370 mg; 1.2 mmol), 3M N-butyl lithium in hexane (0.7 ml; 2.1 mmol) and 1,2,3,4-tetrahydroquinolin-1-carbonyl chloride (300 mg; 1.5 mmol) using the procedure described in example 7 was prepared 50 mg (9%) of the title compound.

Analysis: $C_{26}H_{31}N_4O_2F$, HCl, $2H_2O$
Cal.: C 59.71% H 6.94% N 10.71%
Found: C 59.44% H 6.81% N 10.48%

EXAMPLE 12

1-[3-(3,4-methylenedioxyphenylcarbamoyloxy)-propyl]-4-(6-fluoro-1-methyl -1H-indazol-3-yl)piperidine, hydrochloride Starting from 4-(6-fluoro-1-methyl-1H-indazol-3-yl)-1-(3-hydroxyprop-1-yl)piperidine (291 mg; 1 mmol) and 3,4-methylendioxyphenylisocyanate (326 mg; 2 mmol) using the procedure described in example 8B was prepared the isolated free base of the title compound.

The isolated free base was dissolved in acetone (5 ml). A 2M solution of hydrogen chloride in diethylether (1 ml) was added at room temperature whereby a white precipitate was formed. The solid was collected and air dried to give 150 mg (30%) of the title compound. M.p. 256°–258° C.

EXAMPLE 13

1-[2-(phenyl)-2-(3,4,5-trimethoxyphenylcarbamoyloxy) ethyl] 4-(6-fluoro-1 -methyl-1H-indazol-3-yl)piperidine A. A mixture of 4-(6-fluoro-1-methyl-1H-indazol-3-yl)piperidine (1 g; 4.3 mmol) and phenyloxirane (0.6 g; 5 mmol) in 10 ml acetonitrile was refluxed for 16 h. The cooled reaction mixture was concentrated in vacuo and purified by chromatography on silica gel 60 with ethyl acetate: methanol (9:1, v/v) as eluent. Concentration of the appropriate fractions gave 500 mg (33%) of 1-(2-hydroxy-2-phenyl-ethyl)-4-(6-fluoro-1-methyl-1H -indazol-3-yl)-piperidine.

Analysis: $C_{21}H_{24}N_3FO$
Cal.: C 71.36% H 6.84% N 11.89%
Found: C 70.95% H 7.07% N 11.62%

B. Starting from 1-(2-hydroxy-2-phenyl-ethyl)-4-(6-fluoro-1-methyl-1H -indazol-3-yl)-piperidine (300 mg; 0.85 mmol) and 3,4,5-trimethoxyphenylisocyanate (300 mg; 1.44 mmol) using the procedure described in example 8B was prepared 160 mg (34%) of the title compound.

Analysis: $C_{31}H_{35}N_4FO_5$
Cal.: C 66.18% H 6.27% N 9.96%
Found: C 65.84% H 6,40% N 9.74[{]jf44

EXAMPLE 14

4-(6-Fluoro-1,2-benzisoxazol-3-yl)-1-(3-((6,7-methylenedioxy-1,2,3,4-tetrahydroquinolin -1-yl)carbonyloxy)propyl)piperidine, hydrochloride A. 3-(4,5-methylenedioxy-2-nitrophenyl)acrylic acid (10 g, 42 mmol) in 50 ml dry DMF, 450 ml absolute ethanol and 1.5 ml conc. HCl was reduced catalytically at 1 atm., 22° C., using 1.5 g 5% palladium on carbon to give 6.5 g 6,7-methylenedioxy-1,2,3,4-tetrahydro-2-oxoquinoline as light brown crystals, which was used without further purification.

B. To 6,7-methylenedioxy-1,2,3,4-tetrahydro-2-oxoquinoline (1.0 g, 5 mmol) suspended in 20 ml dioxane at 0° C. was added $NaBH_4$ (1.0 g, 25 mmol) whereupon a mixture of glacial acetic acid (1.4 ml, 25 mmol) in 25 ml dioxane was added dropwise over 10 min. After addition was completed the mixture was refluxed for 1.5 h, concentrated in vacuo and taken up in $H_2O$ and methylene chloride.

The organic phase was dried over $Na_2SO_4$ and evaporated to give 700 mg 6,7-methylenedioxy-1,2,3,4-tetrahydroquinoline as an oil. The oil was taken up in acetone and treated with 1 ml 5.5M HCl in methanol to give 550 mg of the hydrochloride. M.p. 238°–240° C.

C. By the same procedure described in example 1A, 6,7-methylenedioxy -1,2,3,4-tetrahydroquinoline (1.8 g, 10 mmol) was reacted with phosgene to prepare 2.2 g 1-(6,6-methylenedioxy-1,2,3,4-tetrahydroquinoline)carbonyl chloride. M.p. 86°–87° C.

D. By following the procedure described in example 2B, 3-(4-(6-fluoro -1,2-benzisoxazol-3-yl)piperidino)-propanol (15 g, 5.5 mmol) was reacted with 1-(6,6-methylenedioxy-1,2,3,4-tetrahydroquinoline)carbonyl chloride (1.3 g, 5.5 mmol) to give 1.0 g of the title compound. M.p. 165°–166° C.

MS (70 eV): 481 (M+, 42%), 291 (20), 233 (22), 176 (70), 118 (73), 96 (100).

EXAMPLE 15

4-(6-Fluoro-1,2-benzisoxazol-3-yl)-1-(2-((6,7-methylenedioxy-1,2,3,4-tetrahydroquinolin -1-yl)carbonyloxy)ethyl)piperidine, oxalate By following the procedure described in example 2B, 2-(4-(6-fluoro-1,2 -benzisoxazol-3-yl)piperidino)-ethanol (260 mg, 1 mmol) was reached with 1-(6,6 -methylenedioxy-1,2,3,4-tetrahydroquinoline)carbonyl chloride (234 mg, 1 mmol) to give 350 mg of the title compound. M.p. 167°–171 ° C., MS (70 eV): 467 (M+, 100%), 27 (22), 247 (67), 190 (40), 177 (100).

EXAMPLE 16

4-(6-Fluoro-1,2-benzisoxazol-3-yl)-1-(4-((6,7-methylenedioxy-1,2,3,4-tetrahydroquinolin-1-yl)carbonyloxy)butyl)piperidine, oxalate By following the procedure described in example 2B 4-(4-(6-fluoro-1,2 -benzisoxazol-3-yl)piperidino)butanol (290 mg, 1 mmol) was reacted with 1-(6,6-methylenedioxy-1,2,3,4-tetrahydroquinoline)carbonyl chloride (235 mg, 1 mmol) to give 350 mg of the title compound. M.p. 106°–108° C.

MS (70 eV): m/z 495 ($M^+$, 100%), 275 (75), 233 (20), 177 (100).

EXAMPLE 17

4-(6-Fluoro-1,2-benzisoxazol-3-yl)-1-(3-((5,6-methylenedioxyindolin-1-yl)carbonyloxy)-2-phenylpropyl)piperidine, oxalate A. Tropic acid (4.1 g, 25 mmol) in 50 ml 10N NaOH was stirred at 100° C. for 16 h. Upon cooling on ice, 50 ml conc. HCl was added slowly. The formed white crystals were isolated and dried to give 2.7 g 2-phenyl-acrylic acid. M.p. 97°–99° C.

B. 2-phenylacrylic acid (1.8 g, 12 mmol) and 4-(6-fluoro-1,2 -benzisoxazol-3-yl)piperidine (2.4 g, 11 mmol) in 100 ml dry isopropanol was refluxed for 3 h. The mixture was concentrated in vacuo and taken up in water whereupon $NaHCO_3$ was added until pH 8–9. The formed crystals were isolated, washed with ethyl acetate and dried to give 2.0 g 3-(4-(6 -fluoro-1,2-benzisoxazol-3-yl)piperidino-2-phenyl-propanoic acid. M.p. 194°–200° C.

C. To 3-(4-(6-fluoro-1,2-benzisoxazol-3-yl)piperidino)-2-phenylpropanoic acid (1.8 g, 5 mmol) in 25 ml dry toluene, stirred at 0° C., a solution of $LiAlH_4$ in THF (5 ml, 1M, 5 mmol) was added dropwise. 20 min. after addition was completed the mixture was allowed to warm to room temperature for 15 min. whereupon $H_2O$ was added dropwise to precipitate aluminum hydroxide. To the organic phase was added 50 ml ether, and the mixture was washed with water and concentrated in vacuo to get 1.6 g of 3-(4-(6-fluoro -1,2-benzisoxazol-3-yl)piperidino)-2-phenylpropanol as an oil.

MS (70 eV): m/z 35 ($M^+$1, 4%), 233 (100), 190 (30), 96 (35).

D. By following the procedure described in example 2B, 3-(4-(6-fluoro -1,2-benzisoxazol-3-yl)piperidino)propanol (350 mg, 1 mmol) was reacted with 1-(2,3-dihydro-5,6-methylenedioxyindole)carbonyl chloride (150 mg, 0.7 mmol) to give 300 mg of the title compound. M.p. 163°–164° C.

MS (70 eV):m/z 543 ($M^+$, 6%), 353 (25), 233 (100), 204 (30), 163 (37).

EXAMPLE 18

4-(6-Fluoro-1,2-benzisoxazol-3-yl)-1-(3-((5,6-methylenedioxyindolin-1-yl)carbonyloxy)propyl)piperidine, hydrochloride A. Using the general procedure described by R. J. Sundberg and J. P. Laurino (J.Org.Chem. (1984), 49, 249–254) 3,4-methylenedioxyaniline was transformed into 5,6-methylenedioxyindole.

B. 5,6-methylenedioxyindole (1.3 g, 8 mmol) dissolved in 25 ml glacial acetic acid was reduced catalytically (1 atm., 22° C.) using 370 mg $PtO_2$ hydrate to give 550 mg of crude 2,3-dihydro-5,6-methylenedioxyindole which was used without further purification.

C. By following the procedure described in example 1A, 2,3-dihydro -5,6-methylenedioxyindole (570 mg, 3.5 mmol) was reacted with phosgene to give 530 mg of 1-(2,3-dihydro-5,6-methylenedioxyindole)carbonylchloride as a semicrystalline oil.

MS (70 eV): m/z 255 ($M^+$, 100%), 162 (80), 132 (80), 96 (100).

D. By following the procedure described in example 2B, 3-(4-(6-fluoro -1,2-benzisoxazol-3-yl)piperidine)propanol (410 mg, 1.5 mmol) was reacted with 1-(2,3-dihydro-5,6-methylenedioxyindole)carbonyl chloride (450 mg, 2 mmol) to give 200 mg of the title compound. M.p. 208°–21 0° C.

MS (70 eV): m/z 467 ($M^+$, 50%), 261 (80), 233 (50), 162 (56), 132 (80), 96 (100).

EXAMPLE 19

1-[3-(3,4,5-trimethoxyphenylcarbamoyloxy)-propyl]-4-(6-fluoro-1-methyl-1H -indazol-3-yl)piperidine Starting from 4-(6-fluoro-1-methyl-1H-indazol-3-yl)-1-(3-hydroxyprop-1-yl)piperidine (300 mg, 1.03 mmol) and 3,4,5-trimethoxyphenylisocyanate (300 mg, 1.44 mmol) using the procedure described in example 1B was prepared 350 mg (68%) of the title compound. M.p. 85°–88° C.

Analysis: $C_{26}H_{33}N_4O_5F, 0.5H_2O$

Calc.: C 61.28% H 6.72% N 10.99%

Found: C 61.28% H 6.66% N 11.02%

We claim:

1. A compound of formula I wherein

A is a straight or branched saturated hydrocarbon chain having 1–6 carbon atoms which is optionally substituted by $C_{1-6}$-alkoxy, or an unsaturated hydrocarbon chain having 2–6 carbon atoms and one double bond, or when $R^1$ is 6-fluoro-1-methyl-1H-indazol-3-yl, then A is also a straight or branched saturated hydrocarbon chain having 1–6 carbon atoms which is substituted with phenyl;

X is O or NH;

Y is O, S, NH or N—$C_{1-6}$-alkyl;

$R^1$ is 6-fluoro-1,2-benzisoxazol-3-yl, 6-fluoro-1H-indazol-3-yl, or 6-fluoro-1 -methyl-1H-indazol-3-yl;

$R^2$ is $C_{1-6}$-alkyl or phenyl; or, when $R^1$ is 6-fluoro-1-methyl-1H-indazol-3-yl, then $R^2$ is also hydrogen; and R³ is phenyl optionally substituted with $C_{1-6}$-alkyl, halogen, $C_{1-6}$-alkoxy, or perhalomethyl, or R³ is

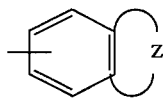

wherein

Z represents a 5- or 6-membered heterocyclic ring comprising one or more nitrogen, oxygen, or sulphur atoms; or R² and R³ together with the nitrogen atom form a dibenzazepine ring system; or a pharmaceutically acceptable salt thereof.

2. A compound according to claim 1, wherein R³ is selected from the group consisting of benzthiazolyl, benzimidazolyl, benzisoxazolyl, 1H-indazolyl, benzofuranyl, indolyl, 3H-indolyl, indolinyl, benzothienyl, quinolinyl, 1,2,3,4-tetrahydroquinolinyl, quinazolinyl and 3,4-methylenedioxyphenyl.

3. A compound according to claim 1, wherein R² and R³ together with the nitrogen atom form a dibenzazepine ring system.

4. A compound according to claim 1, wherein R³ is phenyl optionally substituted with $C_{1-6}$-alkyl, halogen, $C_{1-6}$-alkoxy, or perhalomethyl.

5. A compound according to claim 1, wherein Y is O.

6. A compound according to claim 1, wherein X is O.

7. A compound according to claim 1, wherein A is straight or branched $C_{1-6}$-alkyl.

8. A compound according to claim 1, which is 4-(6-Fluoro-1,2-benzisoxazol-3-yl)-1-(3-(N-ethyl-N-(3,4-methylenedioxyphenyl)carbamoyloxy)propyl)piperidine;

4-(6-Fluoro-1,2-benzisoxazol-3-yl)-1-(3-(N-methyl-N-phenylcarbamoyloxy)propyl)piperidine;

4-(6-Fluoro-1,2-benzisoxazol-3-yl)-1-(3-(N-(6-benzothiazolyl) -N-methylcarbamoyloxy)propyl)piperidine;

4-(6-Fluoro-1,2-benzisoxazol-3-yl)-1-(3-(N-methyl-N-(3,4 -methylenedioxyphenyl)carbamoyloxy)propyl)piperidine; or a pharmaceutically acceptable salt thereof.

9. A compound according to claim 1, which is

1-[2-(3,4,5-trimethoxyphenylcarbamoyloxy)propyl]-4-(6-fluoro-1-methyl-1H -indazol-3-yl)piperidine;

1-[3-(3,4-methylenedioxophenylcarbamoyloxy)propyl]-4-(6-fluoro-1-methyl-1H -indazol-3-yl)piperidine;

1-[2-(phenyl)-2-(3,4,5-trimethoxyphenylcarbamoyloxy)ethyl]-4-(6-fluoro-1 -methyl-1H-indazol-3-yl)piperidine;

1-[3-(3,4,5-trimethoxyphenylcarbamoyloxy)propyl]-4-(6-fluoro-1-methyl-1H -indazol-3-yl)piperidine; or a pharmaceutically acceptable salt thereof.

10. A pharmaceutical composition comprising a compound according to claim 1 and a therapeutically inert excipient, carrier or diluent.

11. A method of treating anxiety, sleep disorders, depression, psychosis, schizophrenia, migraine, ischemic neuronal damage, asthma, hypertension, urticaria, analgesia or emesis, comprising administering to a subject in need thereof an effective amount of a compound according to claim 1.

12. A method of treating anxiety, sleep disorders, depression, psychosis, schizophrenia, migraine, ischemic neuronal damage, asthma, hypertension, urticaria, analgesia or emesis, comprising administering to a subject in need thereof a pharmaceutical composition according to claim 10.

13. A compound which is 4-(6-Fluoro-1,2-benzisoxazol-3-yl)-1-(3-((5,6-methylenedioxyindolin-1 -yl)carbonyloxy)-2-phenylpropyl)piperidine; or a pharmaceutically acceptable salt thereof.

14. A pharmaceutical composition comprising a compound according to claim 13 and a therapeutically inert excipient, carrier or diluent.

15. A method of treating anxiety, sleep disorders, depression, psychosis, schizophrenia, migraine, ischemic neuronal damage, asthma, hypertension, urticaria, analgesia or emesis, comprising administering to a subject in need thereof an effective amount of a compound according to claim 13.

16. A method of treating anxiety, sleep disorders, depression, psychosis, schizophrenia, migraine, ischemic neuronal damage, asthma, hypertension, urticaria, analgesia or emesis, comprising administering to a subject in need thereof a pharmaceutical composition according to claim 14.

17. A compound of formula I

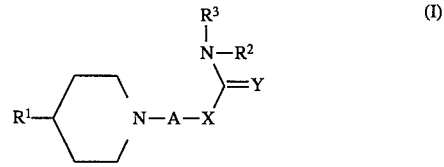

wherein

A is a straight or branched saturated hydrocarbon chain having 1–6 carbon atoms which is optionally substituted by $C_{1-6}$-alkoxy, or an unsaturated hydrocarbon chain having 2–6 carbon atoms and one double bond, or when R¹ is 6-fluoro-1-methyl-1H-indazol-3-yl, then A is also a straight or branched saturated hydrocarbon chain having 1–6 carbon atoms which is substituted with phenyl;

X is O or NH;

Y is O, S, NH or N—$C_{1-6}$-alkyl;

R¹ is 6-fluoro-1,2-benzisoxazol-3-yl, 6-fluoro-1H-indazol-3-yl, or 6-fluoro -1-methyl-1H-indazol-3-yl;

R² and R³ together with the nitrogen atom form an indoline, 1,2,3,4-tetrahydroquinoline, methylenedioxyindoline, methylenedioxy-1,2,3,4-tetrahydroquinoline or a 3,4-dihydro-2H-1,4-benzoxazine ring system; or a pharmaceutically acceptable salt thereof.

18. A compound according to claim 17, which is 4-(6-Fluoro-1,2-benzisoxazol-3-yl)-1-(3-((1,2,3,4-tetrahydroquinolin -1yl)carbonyloxy)propyl)piperidine;

4-(6-Fluoro-1,2-benzisoxazol-3-yl)-1-(2-((1,2,3,4-tetrahydroquinolin -1yl)carbonyloxy)propyl)piperidine;

4-(6-Fluoro-1,2-benzisoxazol-3-yl)-1-(3-((6,7-methylenedioxy -1,2,3,4-tetrahydroquinolin-1-yl)carbonyloxy)propyl)piperidine;

4-(6-Fluoro-1,2-benzisoxazol-3-yl)-1-(2-((6,7-methylenedioxy -1,2,3,4-tetrahydroquinolin-1-yl)carbonyloxy)ethyl)piperidine;

4-(6-Fluoro-1,2-benzisoxazol-3-yl)-1-(4-((6,7-methylenedioxy -1,2,3,4-tetrahydroquinolin-1-yl)carbonyloxy)butyl)piperidine; or a pharmaceutically acceptable salt thereof.

19. A compound according to claim 17, which is 4-(6-Fluoro-1,2-benzisoxazol-3-yl)-1-(3-((indolin-1-yl)carbonyloxy)propyl)piperidine;

4-(6-Fluoro-1,2-benzisoxazol-3-yl)-1-(3-((5,6-methylenedioxyindolin-1-yl)carbonyloxy)propyl)piperidine; or a pharmaceutically acceptable salt thereof.

20. A compound according to claim 17, which is 4-(6-fluoro-1-methyl-1H-indazol-3-yl)-1-(3-((1,2,3,4-tetrahydroquinolin-1-yl)carbonyloxy)propyl)piperidine; or a pharmaceutically acceptable salt thereof.

21. A compound according to claim 17, wherein Y is O.

22. A compound according to claim 17, Wherein X is O.

23. A compound according to claim 17, wherein A is straight or branched $C_{1-6}$-alkyl.

24. A pharmaceutical composition comprising a compound according to claim 17 and a therapeutically inert excipient, carrier or diluent.

25. A method of treating anxiety, sleep disorders, depression, psychosis, schizophrenia, migraine, ischemic neuronal damage, asthma, hypertension, urticaria, analgesia or emesis, comprising administering to a subject in need thereof an effective amount of a compound according to claim 17.

26. A method of treating anxiety, sleep disorders, depression, psychosis, schizophrenia, migraine, ischemic neuronal damage, asthma, hypertension, urticaria, analgesia or emesis, comprising administering to a subject in need thereof a pharmaceutical composition according to claim 24.

27. A compound which is

1-[2((10,11-dihydro-5H-dibenz[b,f]azepin-5-yl)carbamoyloxy)propyl]-4-(6-fluoro-1,2-benzisoxazol-3-yl)piperidine;

1-[3-((10,11-dihydro-5H-dibenz[b,f]azepin-5-yl)carbonyloxy)propyl]-4-(6-fluoro-1,2-benzisoxazol-3-yl)piperidine; or a pharmaceutically acceptable salt thereof.

28. A pharmaceutical composition comprising a compound according to claim 27 and a therapeutically inert excipient, carrier or diluent.

29. A method of treating anxiety, sleep disorders, depression, psychosis, schizophrenia, migraine, ischemic neuronal damage, asthma, hypertension, urticaria, analgesia or emesis, comprising administering to a subject in need thereof an effective amount of a compound according to claim 27.

30. A method of treating anxiety, sleep disorders, depression, psychosis, schizophrenia, migraine, ischemic neuronal damage, asthma, hypertension, urticaria, analgesia or emesis, comprising administering to a subject in need thereof a pharmaceutical composition according to claim 28.

* * * * *